(12) United States Patent
De Araujo et al.

(10) Patent No.: US 11,759,148 B2
(45) Date of Patent: *Sep. 19, 2023

(54) WEARABLE MULTIMODAL-SENSING DEVICE

(71) Applicant: Tactual Labs Co., New York, NY (US)

(72) Inventors: Bruno Rodrigues De Araujo, Toronto (CA); Darren Leigh, Leesburg, VA (US); David Holman, Toronto (CA); David Clark Wilkinson, Austin, TX (US)

(73) Assignee: Tactual Labs Co., New York, NY (US)

(*) Notice: Subject to any disclaimer, the term of this patent is extended or adjusted under 35 U.S.C. 154(b) by 177 days.

This patent is subject to a terminal disclaimer.

(21) Appl. No.: 16/914,258

(22) Filed: Jun. 26, 2020

(65) Prior Publication Data

US 2020/0367820 A1    Nov. 26, 2020

Related U.S. Application Data

(63) Continuation-in-part of application No. 16/910,982, filed on Jun. 24, 2020, and a continuation-in-part of application No. 16/909,608, filed on Jun. 23, 2020, and a continuation-in-part of application No. 16/879,698, filed on May 20, 2020.

(60) Provisional application No. 63/013,507, filed on Apr. 21, 2020, provisional application No. 62/977,132, filed on Feb. 14, 2020, provisional application No. 62/965,425, filed on Jan. 24, 2020, provisional application No. 62/910,528, filed on Oct. 4, 2019, provisional application No. 62/866,809, filed on Jun. 26, 2019, provisional application No. 62/867,006, filed on Jun. 26, 2019, provisional application No.

(Continued)

(51) Int. Cl.
| | |
|---|---|
| *A61B 5/00* | (2006.01) |
| *G06F 3/0488* | (2022.01) |
| *G06F 3/041* | (2006.01) |
| *G06F 3/01* | (2006.01) |

(52) U.S. Cl.
CPC ........... *A61B 5/681* (2013.01); *A61B 5/7257* (2013.01); *G06F 3/017* (2013.01); *G06F 3/0488* (2013.01); *G06F 3/04142* (2019.05)

(58) Field of Classification Search
CPC ............... A61B 5/1126; A61B 5/1107; A61B 5/1125; A61B 5/7228; A61B 5/681; A61B 5/7257; A61B 5/1123; G01H 11/08; G01S 13/50; G01S 7/356; G06F 3/014; G06F 3/0481; G06F 3/04812; G06F 3/017; G06F 3/04142; G06F 3/0488; G06F 2200/1637; G06F 1/163; G06F 1/1694; H01Q 1/273

See application file for complete search history.

(56) References Cited

U.S. PATENT DOCUMENTS

| | | | |
|---|---|---|---|
| 2015/0091790 A1* | 4/2015 | Forutanpour | G06F 3/011 345/156 |
| 2015/0215443 A1* | 7/2015 | Heo | H04M 1/05 455/556.1 |
| 2020/0111260 A1* | 4/2020 | Osborn | G06T 19/006 |

* cited by examiner

*Primary Examiner* — Phuong H Nguyen
(74) *Attorney, Agent, or Firm* — Adam Landa

(57) ABSTRACT

A multimodal sensing system comprises a plurality of sensors placed proximate to a body part. The sensing system receives, using a plurality of sensors, a plurality of signals related to at least one of a movement and a pose of the body part. The sensing system then extrapolates information regarding the type of movement or pose and at least one characteristic of the type a movement or pose.

18 Claims, 11 Drawing Sheets

Related U.S. Application Data

62/866,206, filed on Jun. 25, 2019, provisional application No. 62/866,324, filed on Jun. 25, 2019, provisional application No. 62/851,387, filed on May 22, 2019.

WEARABLE MULTIMODAL-SENSING DEVICE

This application claims the benefit of U.S. Provisional Application No. 62/867,006 filed on Jun. 26, 2019. This application is a continuation-in-part of U.S. patent application Ser. No. 16/910,982 filed on Jun. 24, 2020, which claims the benefit of U.S. Patent Provisional Application No. 62/866,324; a continuation-in-part of U.S. patent application Ser. No. 16/909,608 filed on Jun. 23, 2020, which claims the benefit of U.S. Patent Provisional Application No. 62/866,206. This application also claims the benefit of U.S. Provisional Application No. 63/013,507 filed on Apr. 21, 2020. This application is also a continuation-in-part of U.S. patent application Ser. No. 16/879,698 filed on May 20, 2020, which claims the benefit of U.S. Patent Provisional Application No. 62/851,387. This application also claims the benefit of U.S. Provisional Application 62/866,809 filed on Jun. 26, 2019. This application also claims the benefit of U.S. Provisional Application No. 62/977,132 filed on Feb. 14, 2020. This application also claims the benefit of U.S. Provisional Application No. 62/910,528 filed on Oct. 4, 2019. This application also claims the benefit of U.S. Provisional Application No. 62/965,425 filed on Jan. 24, 2020. The contents of all of the aforementioned applications incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed apparatus and method relate to the field of sensors, in particular the disclosed apparatus and method relate to gesture and human interaction sensors.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

DETAILED DESCRIPTION

Figure 1:
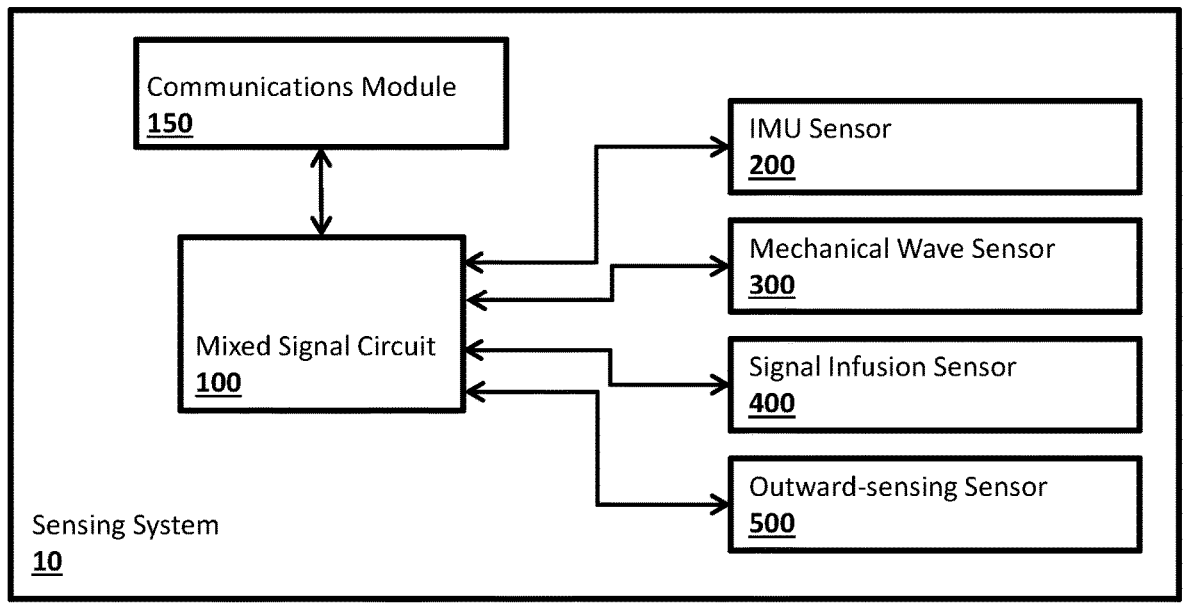
FIG. 1 shows a diagram of a sensing system.

The present application contemplates an improved sensing system implementing a plurality of sensing modalities to characterize a movement or a pose of a body part. In embodiments disclosed herein the improved sensing system can be implemented on a wearable device. Through the use of multiple sensing architectures located strategically with respect to the anatomy of the body part an accurate representation of the body part can be achieved.

The ability to accurately determine what a body part is doing allows for advanced interaction of a user with a computer system. A user of a wearable device may interact with virtual objects by effecting a pinch or a tap that can then be discerned by the sensing system. As used herein, the term "pinch" refers to the act by a user of bringing two fingers in contact with each other. As used herein, the term "touch" refers to the act by a user of bringing a finger into contact with an object or another body part (including other fingers) without the subsequent pressure. As used herein, the term "tap" refers to the act by a user of a user bringing a digit into contact with an or another portion of the body and the time of contact is less than that of a touch. Moreover, the improved sensing systems disclosed herein can determine characteristics of the pose or movement (e.g., force, dwell, or within-contact motion—such as rubbing and sliding) thereby providing more sophisticated data to perfect the human-computer interaction. As used herein, the term "haptic" refers to any device capable of applying forces, vibrations, or motions to a user.

The following scenarios provide a small sampling of the plethora of applications of the improved sensing systems disclosed herein. An architect wearing an AR headset and the improved sensing systems disclosed herein approaches a handmade, physical model of a building her team has designed. She wants to know more about the materials and structural features planned for its walls. She taps her finger to the outside surface of the model, selecting it and bringing up general details, then presses progressively harder to peel away outside layers and reveal the model's internal features radiating from the touch location. A player in an online VR game wishes to customize their character's clothes. In the customization menu they pinch the bottom hem of their character's tunic, then drag it lower for a more dramatic, flowing cut. A spin class instructor is playing music for a session through his mobile phone. Noticing that his students don't seem to be benefitting from a low-energy section of one song, he reaches further around his handlebars to pinch his thumb and forefinger together, rubbing them in clockwise circles to scrub forward through the track.

As noted above and as will be apparent to those skilled in the art, the improved sensing systems disclosed herein may be used in combination with other systems. For instance, augmented reality headsets, virtual reality headsets, mobile devices, wearables/smartwatches, external hand/finger tracking systems, cameras and infrared tracking systems, active or passive handheld props, or conductive or non-conductive surfaces, including touchscreens and computers; among many others. The presently disclosed systems and methods present vast improvements over existing computer vision tracking systems, specifically in low-light or darkness conditions, when the body part is out of view of the tracking system (e.g., in the user's pockets, behind the user's back, or under a table), when interacting with held objects, and when wearing gloves or mittens.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristics. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency orthogonal to each other, in which case, they could not be the same frequency.

Sensing Modalities

The presently disclosed systems and methods involve principles related to and for designing, manufacturing and using capacitive based sensors, signal infusion sensors (also known as signal injection), inertial measurement sensors (including accelerometers, gyroscopes, and magnetometers), pressure-based sensors, microphones, speakers, piezoelectric sensors, and millimeter wave signal-based sensors. Some of the sensing modalities disclosed above may be implemented as microelectromechanical systems (MEMS). As such, this application incorporates by reference Applicant's allowed application U.S. patent application Ser. No. 15/687,401, U.S. Provisional Patent Application No. 62/851,387, and U.S. Provisional Patent Application No. 62/866,809.

The sensing modalities disclosed herein can employ a multiplexing scheme based on orthogonal signaling such as but not limited to frequency-division multiplexing (FDM), code-division multiplexing (CDM), or a hybrid modulation technique that combines both FDM and CDM methods. References to frequency herein could also refer to other orthogonal signal bases. As such, this application incorporates by reference Applicants' prior U.S. Pat. No. 9,019,224, entitled "Low-Latency Touch Sensitive Device" and U.S. Pat. No. 9,158,411 entitled "Fast Multi-Touch Post Processing." These applications contemplate FDM, CDM, or FDM/CDM hybrid touch sensors which may be used in connection with the presently disclosed sensors. As explained in further detail below, in such sensors, interactions are sensed when a signal from a row is coupled (increased) or decoupled (decreased) to a column and the result received on that column. By sequentially exciting the rows and measuring the coupling of the excitation signal at the columns, a heatmap reflecting capacitance changes, and thus proximity, can be created.

Further, this application also employs principles used in fast multi-touch sensors and other interfaces disclosed in the following: U.S. Pat. Nos. 9,933,880; 9,529,476; 9,811,214; 9,804,721; and 9,710,113; U.S. patent application Ser. Nos. 15/162,240; 15/690,234; 15/195,675; 15/200,642; 15/821,677; 15/904,953; 15/905,465; 15/943,221; U.S. Provisional Application Nos. 62/540,458; 62/572,005; 62/621,117; 62/619,656; and PCT Publication PCT/US2017/050547. Familiarity with the disclosure, concepts and nomenclature within these patents is presumed. The entire disclosures of those patents and the applications incorporated therein by reference are incorporated herein by reference.

Certain principles of a fast multi-touch (FMT) sensor have been disclosed in the patent applications discussed above. Orthogonal signals may be transmitted into a plurality of transmitting antennas (or conductors) and information may be received by receivers attached to a plurality of receiving antennas (or conductors). In an embodiment, receivers "sample" the signal present on the receiving antennas (or conductors) during a sampling period ($\tau$). In an embodiment, signal (e.g., the sampled signal) is then analyzed by a signal processor to identify touch events (including, e.g., actual touch, near touch, hover and farther away events that cause a change in coupling between a transmitting antenna (or conductor) and receiving antennas (or conductor)). In an embodiment, one or more transmitting antennas (or conductors) can move with respect to one or more receiving antennas (or conductors), and such movement causes a change of coupling between at least one of the transmitting antennas (or conductors) and at least one of the receiving antennas (or conductors). In an embodiment, one or more transmitting antennas (or conductors) are relatively fixed with respect to one or more receiving antennas (or conductors), and the interaction of the signal and/or signals transmitted with environmental factors causes a change of coupling between at least one of the transmitting antennas (or conductors) and at least one of the receiving antennas (or conductors). The transmitting antennas (or conductors) and receiving antennas (or conductors) may be organized in a variety of configurations, including, e.g., a matrix where the crossing points form nodes, and interactions are detected by processing of received signals. In an embodiment where the orthogonal signals are frequency orthogonal, spacing between the orthogonal frequencies, $\Delta f$, is at least the reciprocal of the measurement period $\tau$, the measurement period $\tau$ being equal to the period during which the column conductors are sampled. Thus, in an embodiment, the received at a column conductor may be measured for one millisecond ($\tau$) using frequency spacing ($\Delta f$) of one kilohertz (i.e., $\Delta f = 1/\tau$).

In an embodiment, the signal processor of a mixed signal circuit (or a downstream component or software) is adapted to determine at least one value representing each frequency orthogonal signal transmitted to (or present on) a row conductor (or antenna). In an embodiment, the signal processor of the mixed signal circuit (or a downstream component or software) performs a Fourier transform on the signals present on a receive antenna (or conductor). In an embodiment, the mixed signal circuit is adapted to digitize received signals. In an embodiment, the mixed signal circuit (or a downstream component or software) is adapted to digitize the signals present on the receive conductor or antenna and perform a discrete Fourier transform (DFT) on the digitized information. In an embodiment, the mixed signal circuit (or a downstream component or software) is adapted to digitize the signals present on the received conductor or antenna and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that the term orthogonal as used herein is not "violated" by such small contributions. In other words, as the term frequency orthogonal is used herein, two signals are considered frequency orthogonal if substantially all of the contribution of one signal to the DFT bins is made to different DFT bins than substantially all of the contribution of the other signal.

When sampling, in an embodiment, received signals are sampled at at least 1 MHz. In an embodiment, received signals are sampled at at least 2 MHz. In an embodiment, received signals are sampled at at least 4 Mhz. In an embodiment, received signals are sampled at 4.096 Mhz. In an embodiment, received signals are sampled at more than 4 MHz. To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmitting antenna. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency orthogonal signal that is transmitted. In an embodiment, each DFT (which can be an FFT) bin comprises an in-phase (I) and quadrature (Q) component. In an embodiment, the sum of the squares of the I and Q components is used as measures corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to activity, touch events, etc. In other words, the measure corresponding to signal strength in a given bin would change as a result of some activity proximate to the sensors, such as a touch event.

The sensing apparatuses discussed herein use transmitting and receiving antennas (also referred to herein as conductors, row conductors, column conductors, transmitting conductors, or receiving conductors). However, it should be understood that whether the transmitting antennas or receiving antennas are functioning as a transmitter, a receiver, or both depends on context and the embodiment. In an embodiment, the transmitters and receivers for all or any combination of the arrangements are operatively connected to a single integrated circuit capable of transmitting and receiving the required signals. In an embodiment, the transmitters and receivers are each operatively connected to a different integrated circuit capable of transmitting and receiving the required signals, respectively. In an embodiment, the transmitters and receivers for all or any combination of the patterns may be operatively connected to a group of integrated circuits, each capable of transmitting and receiving the required signals, and together sharing information necessary to such multiple IC configuration. In an embodiment, where the capacity of the integrated circuit (i.e., the number of transmit and receive channels) and the requirements of the patterns (i.e., the number of transmit and receive channels) permit, all of the transmitters and receivers for all of the multiple patterns used by a controller are operated by a common integrated circuit, or by a group of integrated circuits that have communications therebetween. In an embodiment, where the number of transmit or receive channels requires the use of multiple integrated circuits, the information from each circuit is combined in a separate system. In an embodiment, the separate system comprises a GPU and software for signal processing.

In an embodiment, the mixed signal circuit is adapted to generate one or more signals and send the signals to the transmitting antennas via the transmitter. In an embodiment, the mixed signal circuit is adapted to generate a plurality of frequency orthogonal signals and send the plurality of frequency orthogonal signals to the transmitting antennas. In an embodiment, the mixed signal circuit is adapted to generate a plurality of frequency orthogonal signals and one or more of the plurality of frequency orthogonal signals to each of a plurality of transmit antennas. In an embodiment, the frequency orthogonal signals are in the range from DC up to about 2.5 GHz. In an embodiment, the frequency orthogonal signals are in the range from DC up to about 1.6 MHz. In an embodiment, the frequency orthogonal signals are in the range from 50 KHz to 200 KHz. The frequency spacing between the frequency orthogonal signals should be greater than or equal to the reciprocal of the integration period (i.e., the sampling period).

In an embodiment, the mixed signal circuit (or a downstream component or software) is adapted to determine at least one value representing each frequency orthogonal signal transmitted by a transmitting antenna. In an embodiment, the mixed signal circuit (or a downstream component or software) performs a Fourier transform to the received signals. In an embodiment, the mixed signal circuit is adapted to digitize received signals. In an embodiment, the mixed signal circuit (or a downstream component or software) is adapted to digitize received signals and perform a discrete Fourier transform (DFT) on the digitized information. In an embodiment, the mixed signal circuit (or a downstream component or software) is adapted to digitize received signals and perform a Fast Fourier transform (FFT) on the digitized information.

Multimodal-Sensing Wearable Device

Aspects of the present invention relate to a sensing system comprising a plurality of different sensing modalities used to determine a movement or pose of a body part.

Turning to FIG. 1, a simplified diagram of a sensing system 10 is shown. The sensing system 10 comprises a mixed signal circuit 100 in communication with a communications module 150 and plurality of sensor sub-systems—described in further detail herein. It will be noted that for the sake of clarity the sensor systems described herein have been described as stand alone subsystems. However, in practice the entirety or a portion of these sensor systems may be implemented in the same integrated circuit. In an embodiment, the mixed signal circuit 100 comprises at least one of a processor, a microcontroller, memory, discrete electronic components, power management circuits, and communication modules (e.g., Wi-Fi, Bluetooth, NFC). In an embodiment, the sensing system 10 comprises a power supply (e.g., a battery) and associated power management circuitry both integrated and discrete.

In an embodiment, the sensing system 10 comprises an inertial measurement unit sensor 200. In an embodiment, the inertial measurement unit (IMU) sensor 200 comprises at least one of an accelerometer 210, a gyroscope, and a magnetometer. In an embodiment, the inertial measurement unit sensor 200 comprises a plurality of at least one of an accelerometer, a gyroscope, a magnetometer, and a combination thereof. In an embodiment, the inertial measurement unit sensor 200 comprises at least one haptic motor.

In an embodiment, the sensing system 10 comprises a mechanical wave sensor 300. In an embodiment, the mechanical wave sensor 300 comprises devices adapted to transmit (e.g., speakers, haptic motors) 310 and receive (e.g., microphones, inertial measurement unit sensors) 320 mechanical waves. In an embodiment, the mechanical wave sensor 300 comprises a MEMS microphone. In an embodiment, the mechanical wave sensor 300 works by receiving the mechanical waves generated or transmitted by the user's body upon excitation of a body part. As will be noted by those skilled in the art different body parts have different resonant frequencies that are generated when those body parts are excited. Those signals generated by the different body parts then received by the mechanical wave sensor. In an embodiment, mechanical waves are transmitted (e.g., by using speakers or haptic motors) to the body and the propagated or reflected signal is received (e.g., by microphones or IMU sensors).

In an embodiment, the sensing system 10 comprises a signal infusion sensor 400. In an embodiment, the signal infusion sensor 400 comprises transmitters 410 adapted to transmit a plurality of signals into the user. The signal infusion sensor 400 further comprises receivers 420 adapted to receive the plurality of signal and to extrapolate information regarding a movement or a pose of a body part from the differences between the transmitted and the received signals.

In an embodiment, the sensing system 10 comprises an outward-sensing sensor 500. In an embodiment, outward-sensing sensor 500 comprises transmitters 510 adapted to transmit a plurality of signals which are then reflected by the body part and received by the receivers 520. The outward-sensing sensor 500 is further adapted to extrapolate information regarding a movement or a pose of a body part from the differences between the transmitted and the received signals.

Further discussion regarding the implementation of the transmitting antennas (or conductors) and receiving antennas (or conductors) in association with wearables can be found in U.S. patent application Ser. No. 15/926,478, U.S. patent application Ser. No. 15/904,953, U.S. patent application Ser. No. 16/383,090 and U.S. patent application Ser. No. 16/383,996, the contents of all of the aforementioned applications incorporated herein by reference.

It will be understood that the embodiments mentioned above are only for illustrative purposes. The sensing system 10 can utilize a multitude of sensing modalities including those disclosed in the Patents and Application incorporated by reference herein.

In an embodiment, the sensing system 10 uses the plurality of sensor sub-systems to create a comprehensive model of the body part being measured by fusing the data from each sensor. As will be understood by those skilled in the art, the sensor modalities disclosed herein and incorporated by reference are complimentary.

As will be further understood, each of the sensing modalities disclosed herein and incorporated by reference provides unique information that allows the sensing system 10 to determine specific characteristics of a movement or a pose effected by a body part. In an embodiment, one sensor can determine the start of an event, while another can determine the duration, force, etc. As a non-limiting example, one sensing modality may detect the initial interaction (e.g., using IMU sensors) between a digit and another body part thereby creating a time boundary in which another sensing modality (e.g., outward-sensing) determines a characteristic (e.g., force or dwell) to draw a conclusion about the interaction (e.g., whether it is a touch, a tap, or a pinch).

Figure 2:
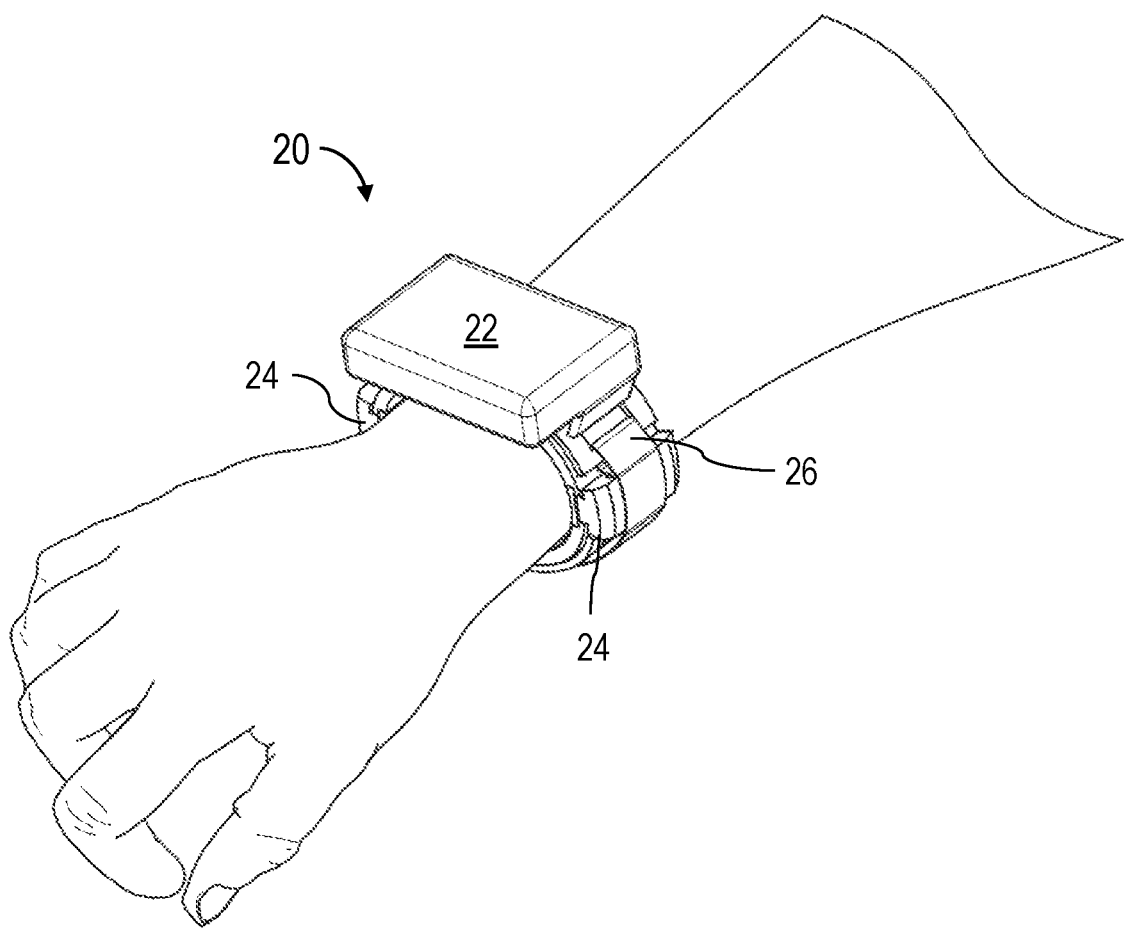
FIG. 2 illustrates a sensing system incorporated into a wearable worn around the wrist of a user.
Figure 3:
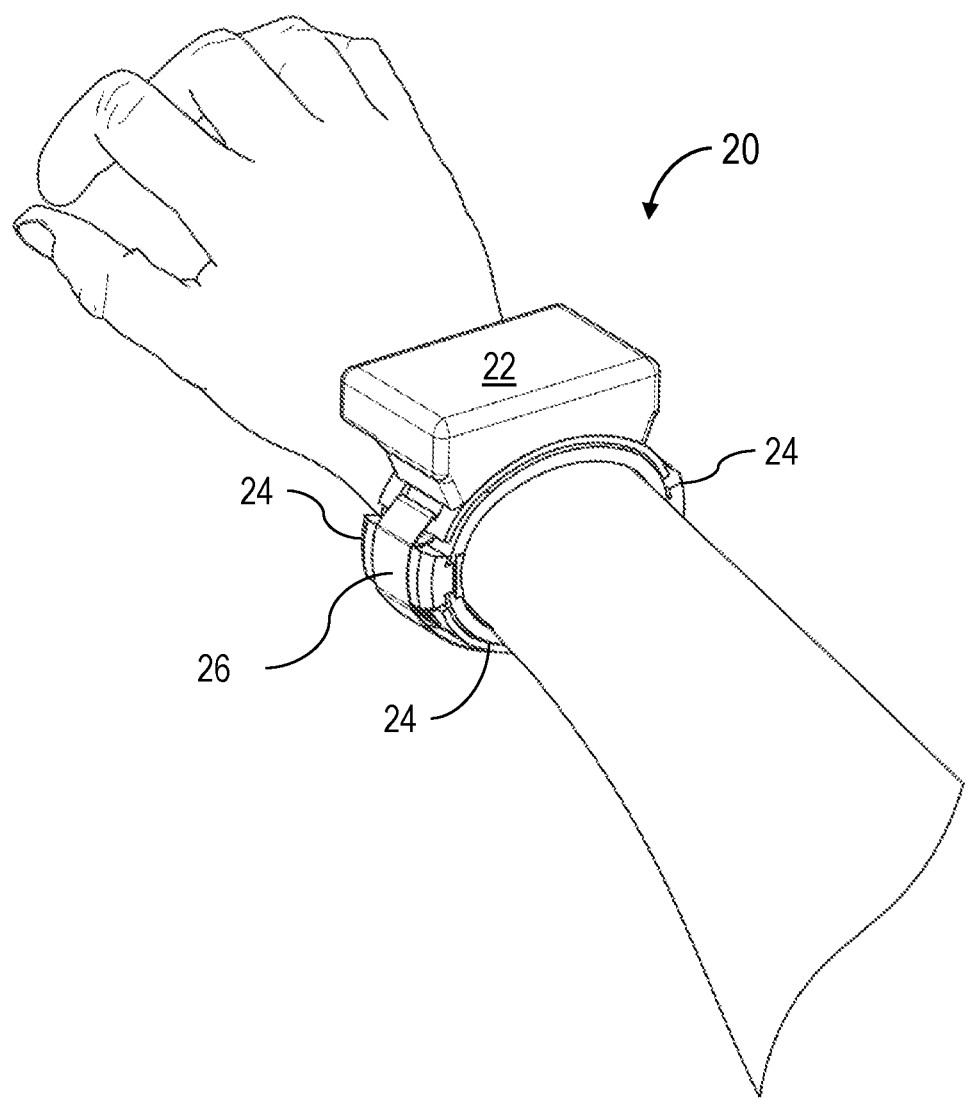
FIG. 3 illustrates a sensing system incorporated into a wearable worn around the wrist of a user.

Turning now to FIGS. 2 and 3, an embodiment of a sensing system 10 incorporated into wearable 20 worn around the wrist of a user is shown. The wearable device 20 comprises a housing 22, at least one secondary housing 24, and a strap 26. In an embodiment, the wearable device 20 comprises only one housing. In an embodiment, the housing is capable of deforming around a body part of a user. As will be discussed in further detail below, embodiments disclosed herein are not limited to any specific body part. In an embodiment the wearable device may be secured around any body part (e.g., ankles, feet, arms, chest, legs, neck, waist, and hands).

In an embodiment, at least one of the mixed signal circuit 100, the communications module 150, the IMU sensor 200, the mechanical wave sensor 300, the signal infusion sensor 400, and the outward-sensing sensor 500 is contained within at least one of the housing 22 and the at least one secondary housing 24.

Figure 4:
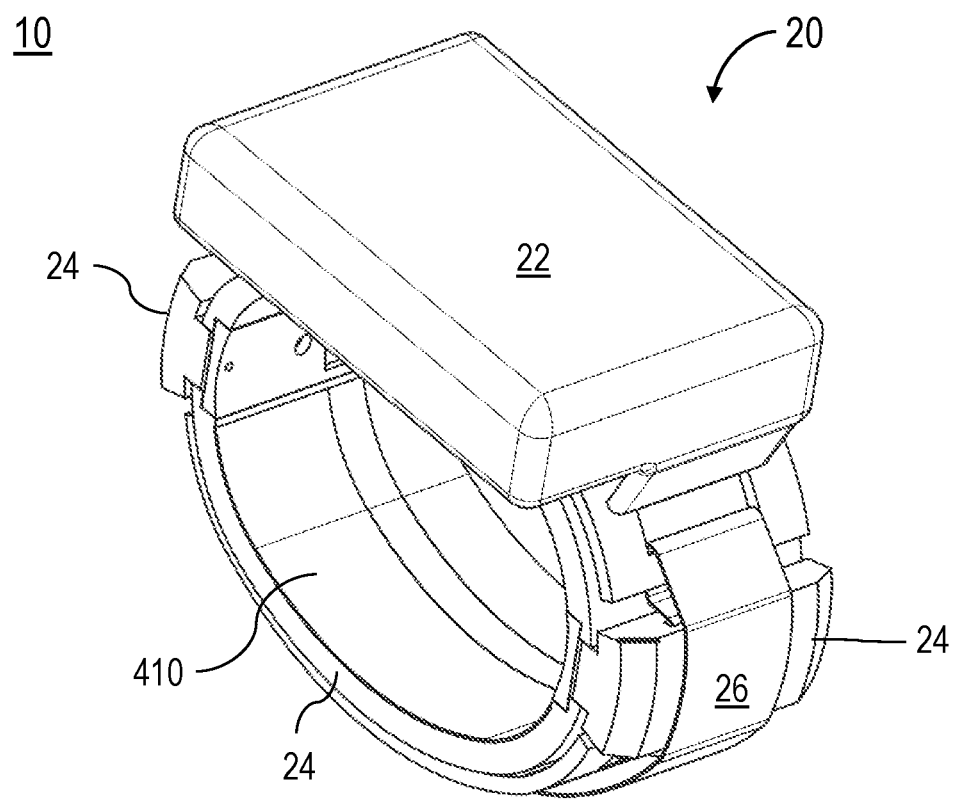
FIG. 4 illustrates a sensing system incorporated into a wearable.
Figure 5:
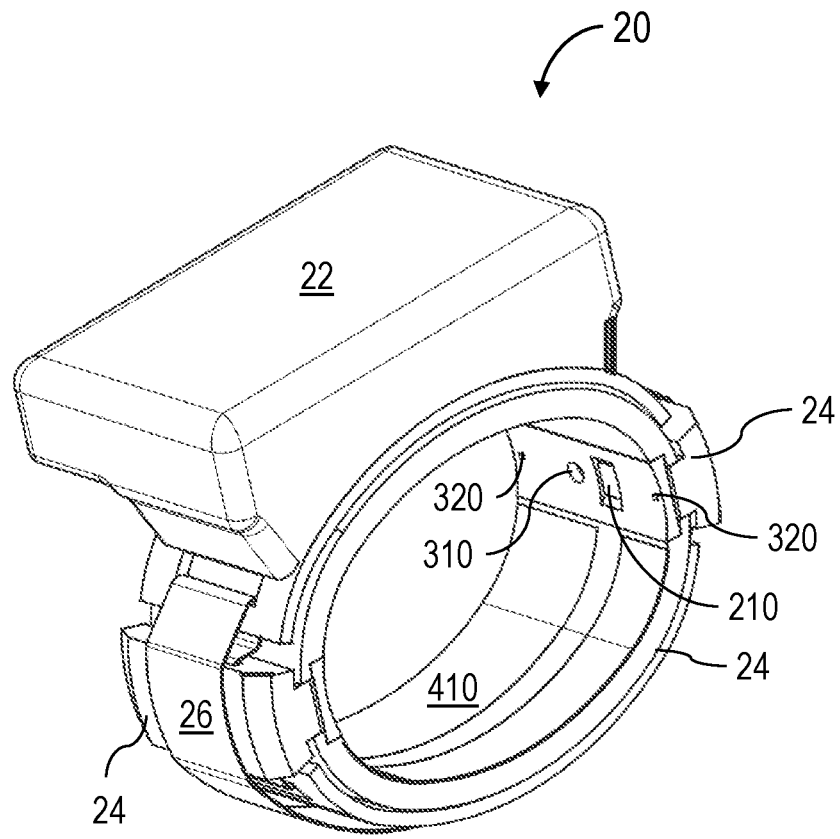
FIG. 5 illustrates a sensing system incorporated into a wearable.

FIGS. 4 and 5 illustrate an embodiment of a sensing system 10 incorporated into wearable 20. In an embodiment, portions of the IMU sensor 200 (not shown), the mechanical wave sensor 300 (not shown), and the signal infusion sensor 400, are housed in the secondary housing 24. In an embodiment, accelerometers of the IMU, MEMS microphones, and speakers sensor are located on the secondary housings 24 proximate to the radius and ulna bones.

Figure 6:
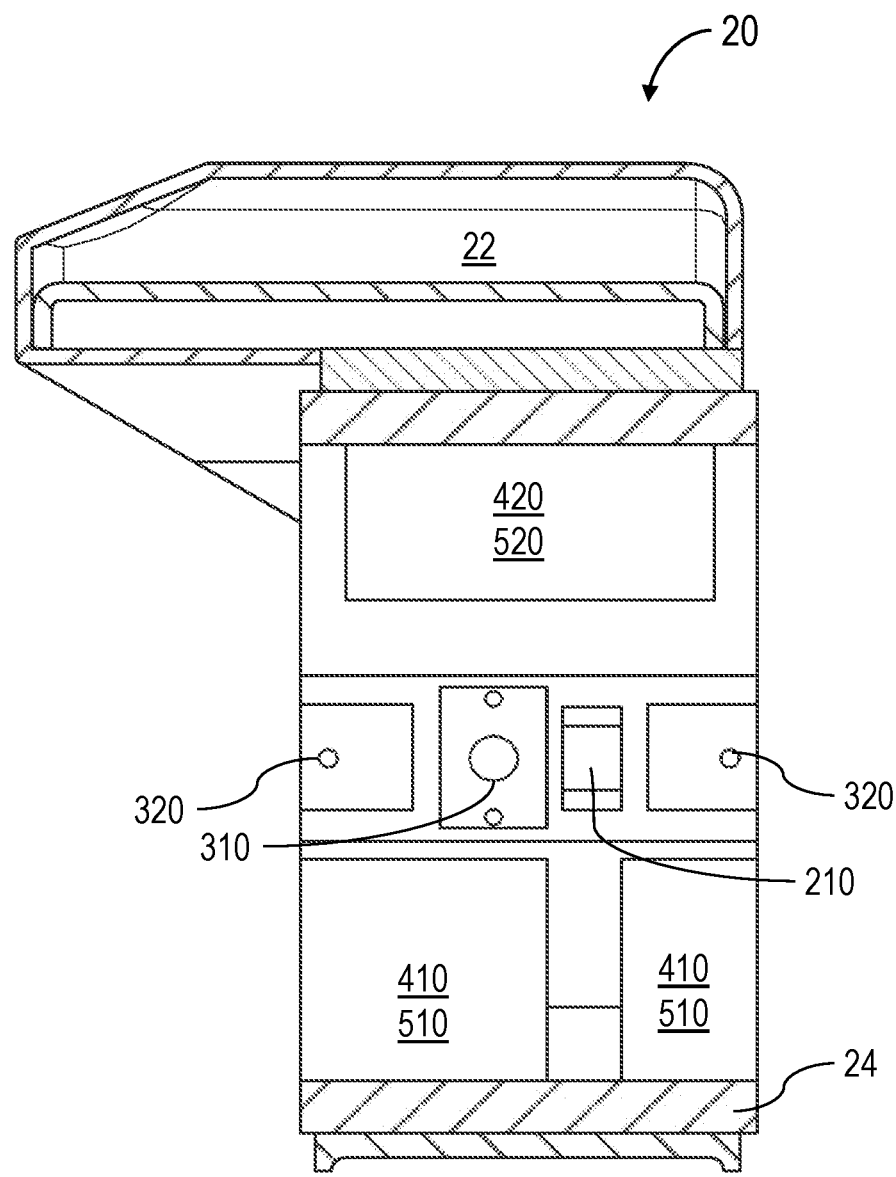
FIG. 6 illustrates a cutaway view of a sensing system incorporated into a wearable 20.

Turning now to FIG. 6, a cutaway view of the sensing system 10 incorporated into the wearable 20 is shown. In an embodiment, the sensing system 10 comprises transmitters 410 and 510 located in secondary housing 24 proximate to the anterior of the wrist. In an embodiment, the sensing system 10 comprises receivers 420 and 520 located in the housing 22 proximate to the posterior of the wrist. In an embodiment, the sensing system 10 comprises at least one speaker 310, at least two microphones 320, and at least one accelerometer 210 located in a housing 24 proximate to the radius on one side and the ulna on the other side.

Figure 7:
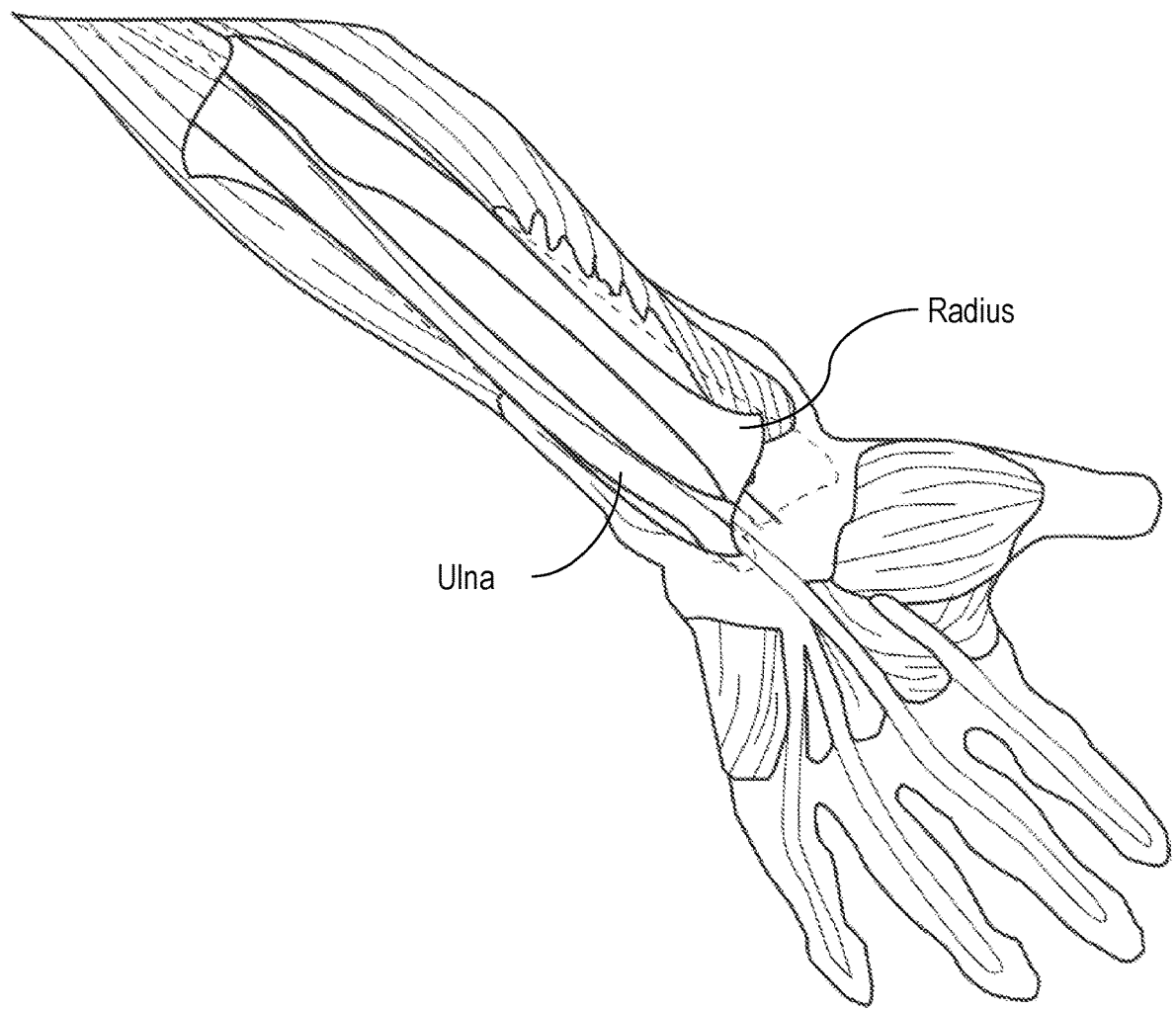
FIG. 7 is a diagram illustrating the musculature of the arm.

FIG. 7 shows a diagram of the musculature in the forearm of a person. The placement of sensors around the wrist is determined by how a particular movement of the hand and fingers manifests in the associated anatomy. In addition, resonance from the excitation of the bones, muscles, and other anatomy propagates to other parts of the anatomy. In an embodiment, excitation of the fingers (e.g., by tapping, pinching, or touching) can be detected at the wrist.

Figure 8:
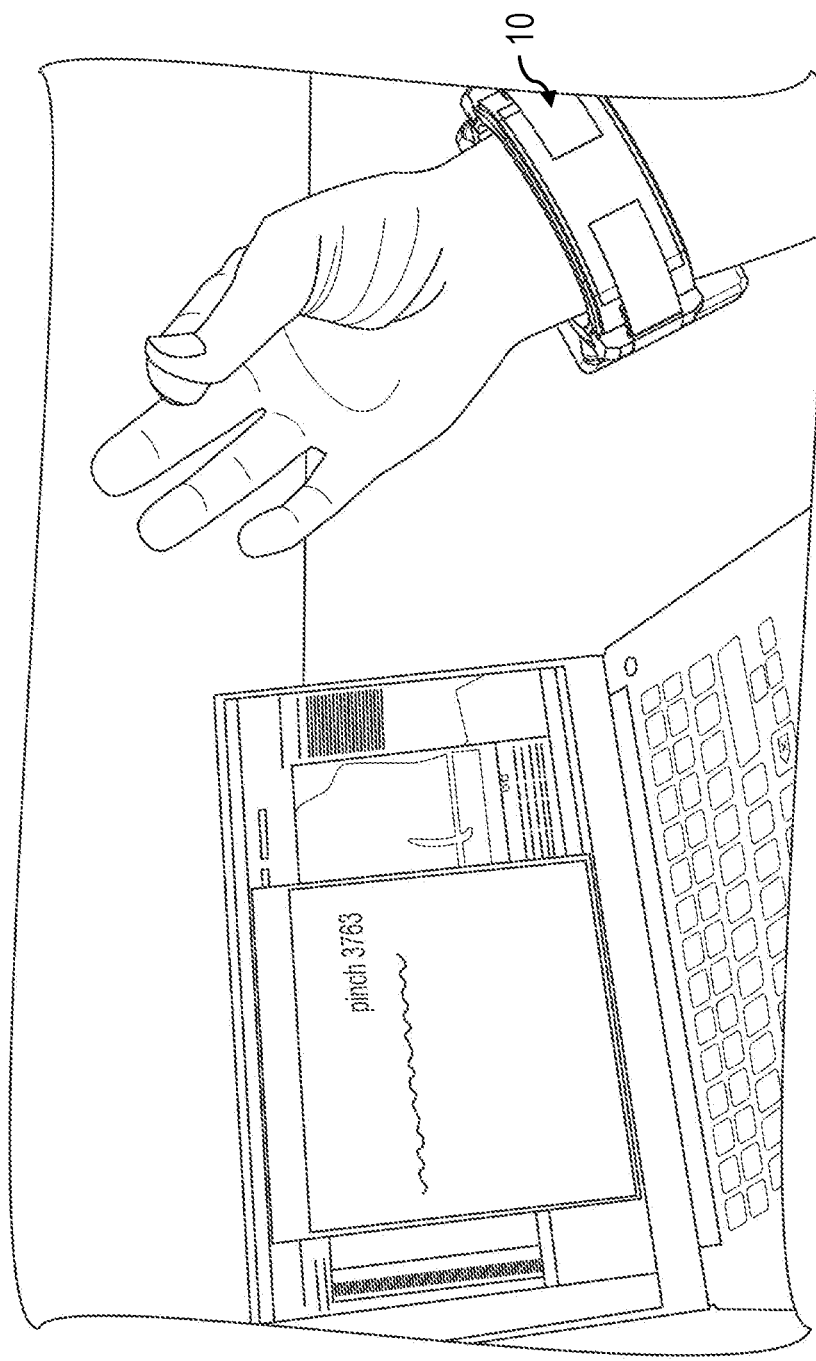
FIG. 8 shows a pinch being determined by a sensing system.
Figure 9:
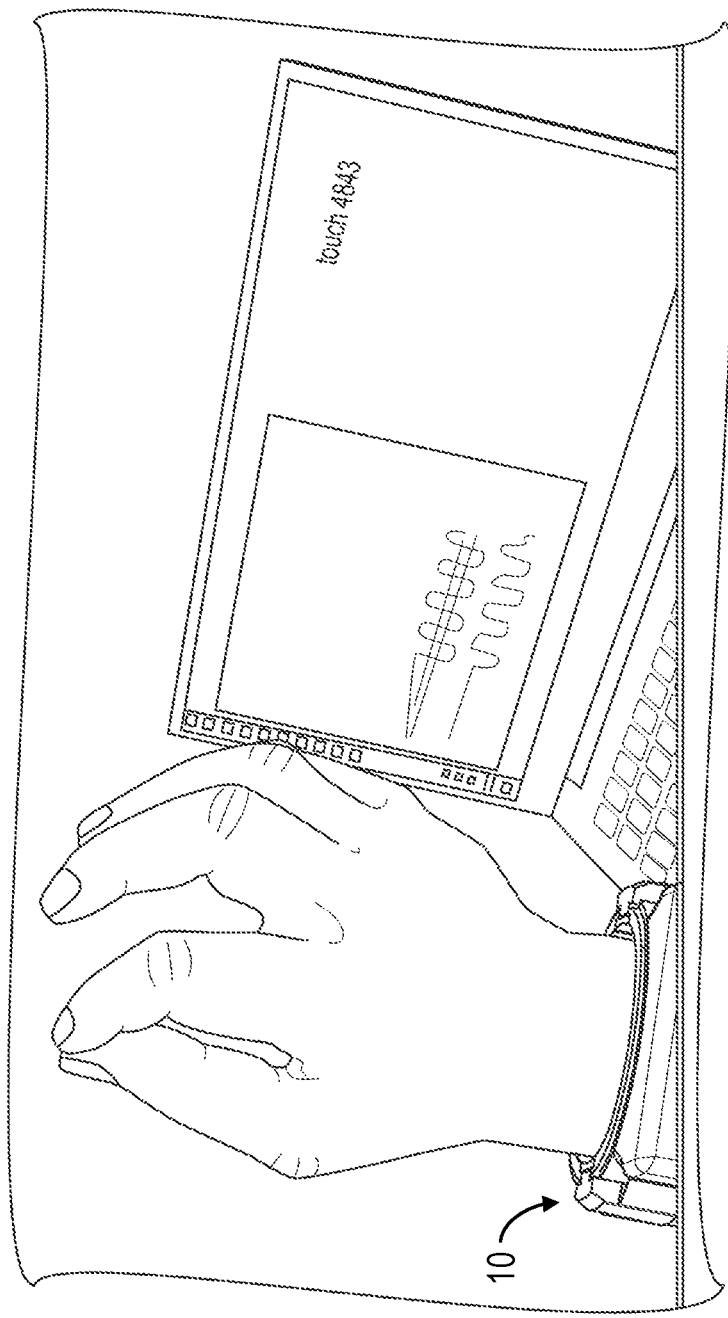
FIG. 9 shows a touch of the fingertips being determined by the sensing system.

FIG. 8 shows a pinch between the index finger and the thumb being detected by the sensing system 10. FIG. 9 shows a touch between the index finger and the thumb being determined by the sensing system 10. The placement of the sensors proximate to those muscles that govern the activity of pinch and touch has been determined to be effective for detecting the internal movements within the wrist area that can be correlated to pinching, tapping, and touching. Thus, the movement and position of physical structure of bones, tendons, veins, arteries, etc. within the wrist area are leveraged by the sensing system 10 to determine the motion of the fingers and determine other hand related behaviors. Additionally, the placement of the sensing system 10 to correlate with musculature, bone, tendon and/or ligament activity that determine other activities of the hands also facilitates such determinations.

Figure 10:
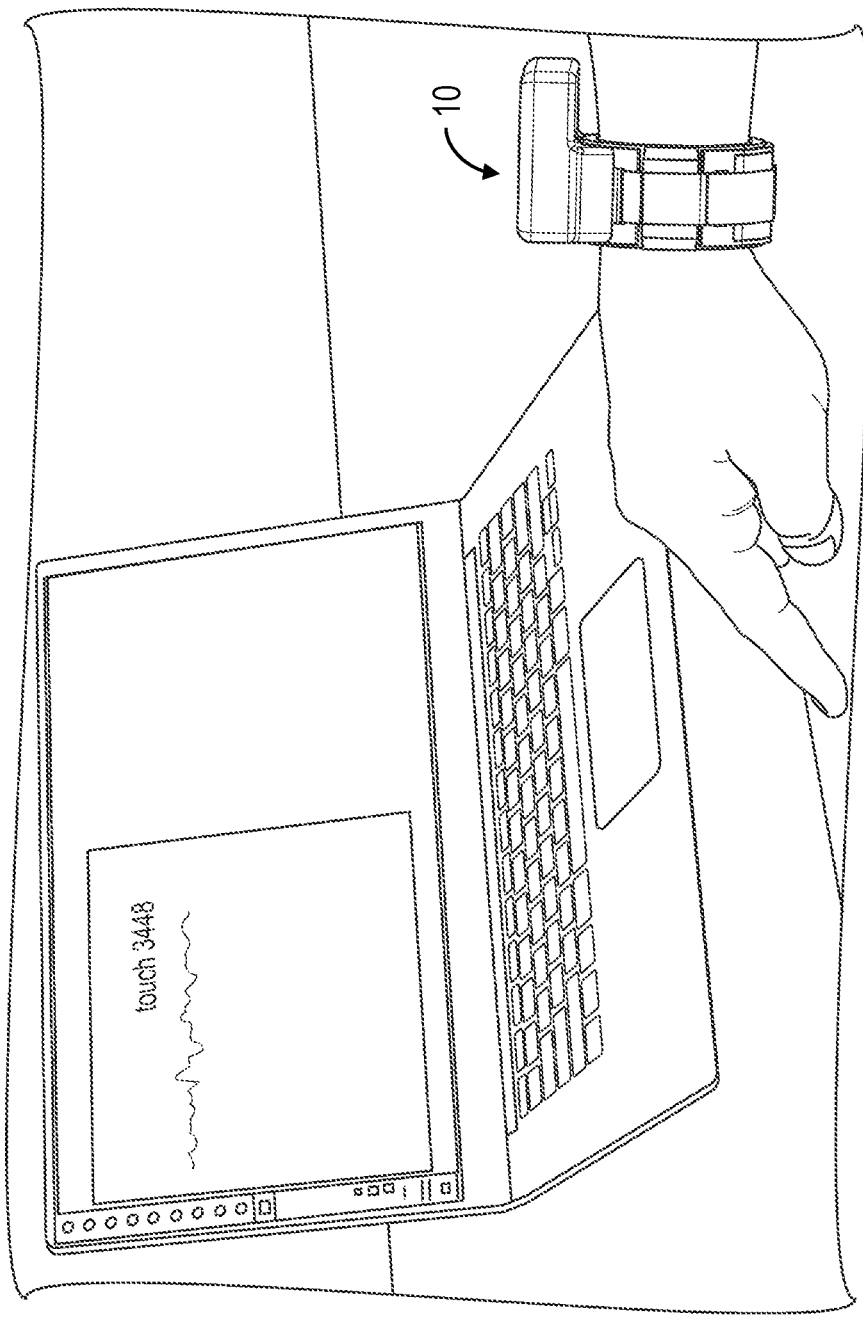
FIG. 10 shows a touch of a table being determined by the sensing system.
Figure 11:
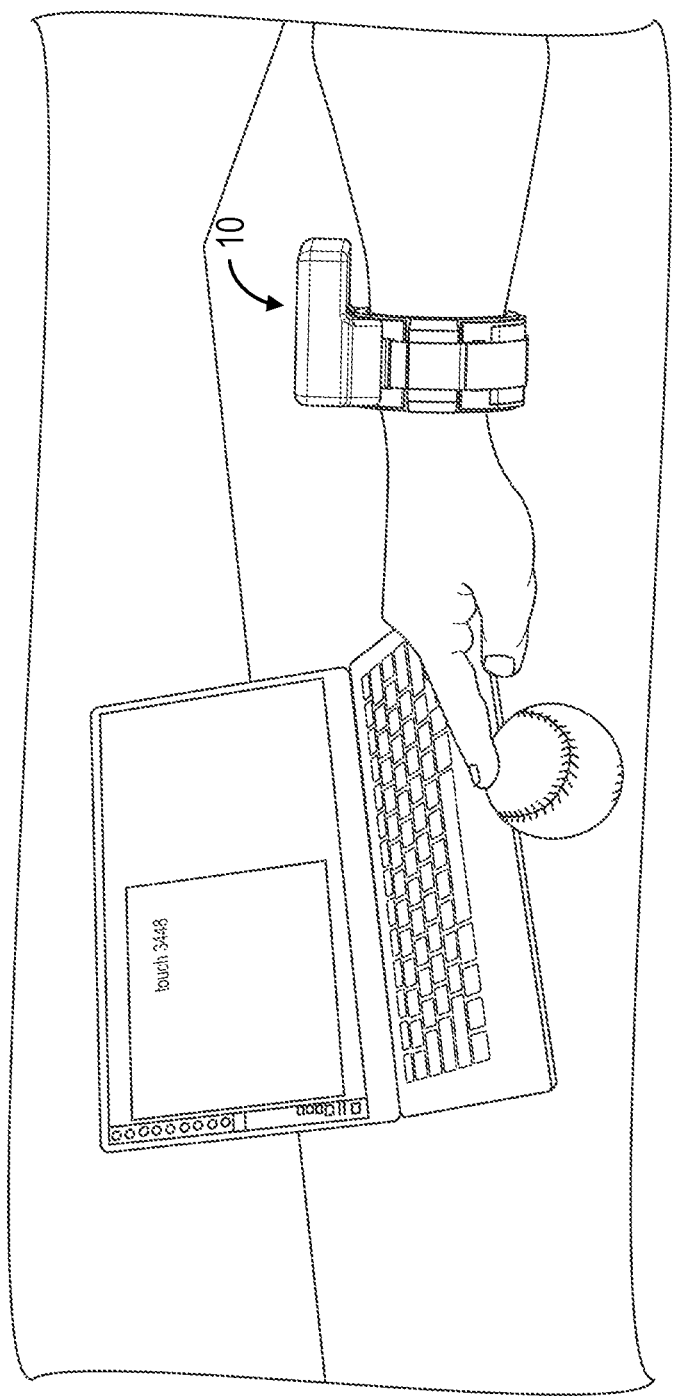
FIG. 11 shows a touch of a baseball being determined by the sensing system.

FIG. 10 shows a touch of a table being determined by the sensing system 10. FIG. 11 shows a touch of a baseball being determined by the sensing system 10. In both situations the touch event is being determined by contact of the finger with the surface of an object and resultant impact that the touch event has on the underlying physical structure within the wrist area.

While wearables used with various body parts are discussed above, principles discussed above with respect to the various embodiments may be used by one of ordinary skill in view of this disclosure to further implement the sensing system discussed above into other wearables.

In an embodiment, the sensing system is implemented in a wearable placed on the ankle. The placement of the sensing system's transmitting antennas and receiving antennas to correlate with musculature, bone, tendon and/or ligament activity that determine activities of the foot provides enhanced measurements of the foot activity. In an embodiment, the sensing system is implemented in a wearable placed on the arm. The placement of the sensing system's transmitting antennas and receiving antennas to correlate with musculature, bone, tendon and/or ligament activity that determine activities associated with the arm provides enhanced measurements of arm activity. In an embodiment, the sensing system is implemented in a sensing device placed on the chest. The placement of the sensing system's transmitting antennas and receiving antennas to correlate with musculature, bone, tendon and/or ligament activity that determine activities associated with the chest (e.g., breathing, heart rate, etc.) provides enhanced measurements of the associated chest activity. In an embodiment, the pressure adaptive sensor system is implemented in a wearable placed on the leg. The placement of the sensing system's transmitting antennas and receiving antennas to correlate with musculature, bone, tendon and/or ligament activity that determine activities associated with the leg provides enhanced measurements of leg activity. In an embodiment, the sensing system is implemented in a wearable placed on the head. The placement of the sensing system's transmitting antennas and receiving antennas to correlate with musculature, bone, tendon and/or ligament activity that determine activities associated with the head provides enhanced measurements of facial activity and head motion. In an embodiment, the sensing system is implemented in a wearable placed on the neck. The placement of the sensing system's transmitting antennas and receiving antennas to correlate with musculature, bone, tendon and/or ligament activity that determine activities associated with the neck provides enhanced measurements of vocalization, breathing, and other associated activities. In an embodiment, the pressure adaptive sensing system is implemented in a wearable placed on the waist. The placement of the sensing system's transmitting antennas and receiving antennas to correlate with musculature, bone, tendon and/or ligament activity that determine activities associated with the waist provide enhanced determination of movement and other associated activities. In an embodiment, the sensing system is implemented in a wearable placed on the hand. The placement of the sensing system's transmitting antennas and receiving antennas to correlate with musculature, bone, tendon and/or ligament activity that determine activities associated with the hand provides enhanced determination of fine hand movement. In an embodiment, the sensing system is implemented in a wearable placed on the foot. The placement of the sensing system's transmitting antennas and receiving antennas to correlate with musculature, bone, tendon and/or ligament activity that determine activities associated with the foot provides enhanced determination of fine foot movement.

An aspect of the disclosure is a multimodal sensing system. The multimodal sensing system, comprising a plurality of sensors operably located within a housing, wherein the housing is adapted to be placed proximate to a body part, the plurality of sensors adapted to receive a plurality of signals related to at least one of a movement and a pose of the body part; and, a processor operably connected to the plurality of sensors, wherein the processor is adapted to receive information from each of the plurality of sensors, and to process the information to determine a type of the at least one of a movement and a pose and at least one characteristic of the type of the at least one of a movement and a pose.

Another aspect of the disclosure is a method for sensing movement of a body part using a multimodal sensing system. The method comprising placing a housing proximate to a body part, wherein operably located within the housing is a plurality of sensors and a processor, wherein the processor is operably connected to the plurality of sensors; receiving a plurality of signals related to at least one of a movement and a pose of the body part using the plurality of sensors; processing using the processor at least one of the plurality of signals; and, determining a type of the at least one of a movement and a pose and at least one characteristic of the type of the at least one of a movement and a pose.

While the invention has been particularly shown and described with reference to a preferred embodiment thereof, it will be understood by those skilled in the art that various changes in form and details may be made therein without departing from the spirit and scope of the invention.

The invention claimed is:

1. A multimodal sensing system, comprising:
a plurality of sensors operably located within a housing, wherein the housing is adapted to be placed proximate to a body part, the plurality of sensors adapted to transmit and infuse signals to a user wherein each of the infused signals is orthogonal from each other signal infused to the user, and then receive the transmitted signals; and,
a processor operably connected to the plurality of sensors, wherein the processor is adapted to receive information from each of the plurality of sensors, and to process the information to determine a type of the at least one of a movement and a pose and at least one characteristic of the type of the at least one of a movement and a pose.

2. The sensing system of claim 1, wherein the body part is a wrist.

3. The sensing system of claim 2, wherein the type of the at least one of a movement and a pose is a pinch.

4. The sensing system of claim 2, wherein the type of the at least one of a movement and a pose is a touch.

5. The sensing system of claim 2, wherein the type of the at least one of a movement and a pose is a tap.

6. The sensing system of claim 1, further comprising infusing a signal into the body part.

7. The sensing system of claim 1, further comprising transmitting a mechanical signal.

8. The sensing system of claim 1, wherein the at least one signal received is processed using a Fast Fourier Transform.

9. The sensing system of claim 1, wherein the at least one characteristic is at least one of a force, a dwell time, and a within-contact motion.

10. A method for sensing movement of a body part using a multimodal sensing system, comprising:
placing a housing proximate to a body part, wherein operably located within the housing is a plurality of sensors and a processor, wherein the processor is operably connected to the plurality of sensors;
transmitting at least one signal from the multimodal sensing system and infusing signals to a user wherein each of the infused signals is orthogonal from each other signal infused to the user;
receiving a plurality of signals related to at least one of a movement and a pose of the body part using the plurality of sensors from the multimodal sensing system;
processing using the processor at least one of the plurality of signals; and,
determining a type of the at least one of a movement and a pose and at least one characteristic of the type of the at least one of a movement and a pose.

11. The method of claim 10, wherein the body part is a wrist.

12. The method of claim 11, wherein the type of the at least one of a movement and a pose is a pinch.

13. The method of claim 11, wherein the type of the at least one of a movement and a pose is a touch.

14. The method of claim 11, wherein the type of the at least one of a movement and a pose is a tap.

15. The method of claim 10, further comprising, prior to the step of receiving, infusing a signal into the body part.

16. The method of claim 10, further comprising, prior to the step of receiving, transmitting a mechanical signal.

17. The method of claim 10, wherein the at least one signal received is processed using a Fast Fourier Transform.

18. The method of claim 10, wherein the at least one characteristic is at least one of a force, a dwell time, and a within-contact motion.

\* \* \* \* \*